United States Patent [19]

Laver

[11] Patent Number: Plant 6,859

[45] Date of Patent: Jun. 20, 1989

[54] ROSE PLANT NAMED 'LAVJUNE'

[75] Inventor: Keith Laver, Caledon East, Canada

[73] Assignee: Nor'East Miniature Roses, Inc., Rowley, Mass.

[21] Appl. No.: 159,042

[22] Filed: Feb. 22, 1988

[51] Int. Cl.[4] ..... A01H 5/00

[52] U.S. Cl. ..... Plt./7

[58] Field of Search ..... Plt. 7

*Primary Examiner*—James R. Feyrer

*Attorney, Agent, or Firm*—Vincent G. Gioia

[57] ABSTRACT

A new unusual bright orange yellow miniature rose of excellent exhibition form.

1 Drawing Sheet

The present invention relates to a new and distinct variety of rose plant of the miniature rose class, which was originated by my crossing as seed parent the variety known as "Helmut Schmidt" and as pollen parent the rose known as "Gold Mine." The denomination of this new rose is "Lavjune."

Among the novel characteristics possessed by this new variety which distinguish it from its parents and all other varieties of which I am aware are its unusual bright orange yellow flowers in this class of rose. Flowers have good exhibition form and are long lasting on the plant and after cutting. Asexual reproduction by budding of the new variety as performed in San Bernardino County, Calif., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Colour Chart (RHSCC). The terminology used in color description herein refers to plate numbers in the aforementioned color chart, e.g., "19C" is plate 19C of the Royal Horticultural Society Colour Chart.

Parentage: Seedling.

*Seed parent.*—"Helmut Schmidt".

Pollen parent.—"Gold Mine".

Class: Miniature.

The following observations are made of specimens grown outdoors in San Bernardino County, Calif., during the month of November.

FLOWER

Blooming habit: Nearly continuous.

A. Bud:

(1) *Size.l —Large.*

(2) *Form.*—Pointed.

(3) *Color.*—As sepals divide, bud color is near Indian Yellow 19C to 19A with yellowish washing toward point of petal attachment.

(4) *Sepals.*—Slightly foliaceous, some with appendages, considerably longer than bud.

(5) *Peduncle.*—Length — about 1 to 1½ inches. Aspect — straight. Strength — erect. Color — near 144A.

B. Bloom:

(1) *Size.*—Average size when fully expanded — about 1¾ to 2 inches.

(2) *Borne.*—Singly, one to a stem and in sprays of three to four blooms.

(3) *Form.*—High centered at first, exhibition blooms retaining form until fully open then becoming flat. Outer petals reflex and quill to points and petal edges roll under.

(4) *Petalage.*—Number of petals under normal conditions — about 20–25.

(5) *Color.*—After sepals divide, initial color visible is a pale yellowish green; but after sepals fall, color of petal undersurface which may be seen is near Indian Yellow 19C with orange overtones. Deeper yellow tonality may be seen near point of petal attachment and pale orange coloring appears at and near petal edges. As flowers open, coloring becomes a beautiful brilliant orange yellow in the range from Nasturtium Orange near 25D to near 25B to Tangerine Orange near 24D to near 24B. During the ⅓ to ½ open stage, deeper orange tonality, e.g., near 25B to 24B, appears at flower centers where petals bunch. Outer petals in the ½ open bloom appear slightly lighter toned. The beautiful bright orange coloring is retained through opening and fades to paler tones near 14D after flowers age. To the human eye, the general tonality appears as a bright orange yellow.

C. Petals:

(1) *Texture.*—Thick.

(2) *Appearance.*—Inside velvety and outside satiny.

(3) i Form.—Broad, fan shaped, outer petals quill to points; inner petals roll under.

(4) *Arrangement.*—Regularly arranged.

(5) *Petaloids in center.*—Few to none.

(6) *Persistence.*—Drop off cleanly.

(7) *Fragrance.*—Slight.

(8) *Lasting quality.*—Very long lasting quality on plant and as cut flower.

REPRODUCTIVE ORGANS

A. Stamens, filaments and anthers:

*Arrangement and color.*—Regularly arranged around styles. Color — filaments near 21C.

B. Pollen:

*Color.*—Near 21C.

C. Styles: Uneven, medium length, bunched, thick.

D. Stigmas:

*Color.*—Near 10A.

E. Hips: Round tapering to base at stem, light orange red.

PLANT

A. Form: Upright, bushy.

B. Growth: Vigorous, uniform branching.

*Height attained.*—About 14 to 18 inches.

C. Foliage: Compound 5 leaflets.

(1) *Size.*—Large.

(2) *Quantity.*—Abundant.

(3) *Color.*—New foliage: Upper side — near 146B. Under side — near 146C. Old foliage: Upper side — near 147A. Under side — near to 147C.

(4) *Shape.*—Oval, pointed.

(5) *Texture.*—Upper side is semiglossy; under side is matte.

(6) *Edge.* —Serrate.

(7) *Serration.*—Ordinary.

(8) *Leaf stem.*—Color — near to 146B.

(9) *Stipules.*—Medium length, slightly bearded.

(10) *Resistance to disease.*—Blackspot — Average. Mildew — Average. Rust — Average.

D. Wood:

(1) *New wood.*—Color — green with reddish cast. Bark — smooth.

(2) *Old wood.*—Color — near 146C. Bark — smooth.

E. Thorns:

(1) *Thorns.*—Quantity (main stalk) — ordinary. On laterals from stalk — ordinary. Form — long, thin, straight, slanted slightly downward. Length — medium. Color — purplish green. Position — irregular.

(2) *Prickles.*—Small, short, sharp.

F. Winter hardiness: Needs protection in severe climates.

I claim:

1. A new and distinct variety of rose plant of the miniature rose class and all parts thereof, substantially as shown and described, characterized particularly by unusual attractive bright orange yellow colored flowers of excellent exhibition form which are long lasting on the plant and as cut flowers.

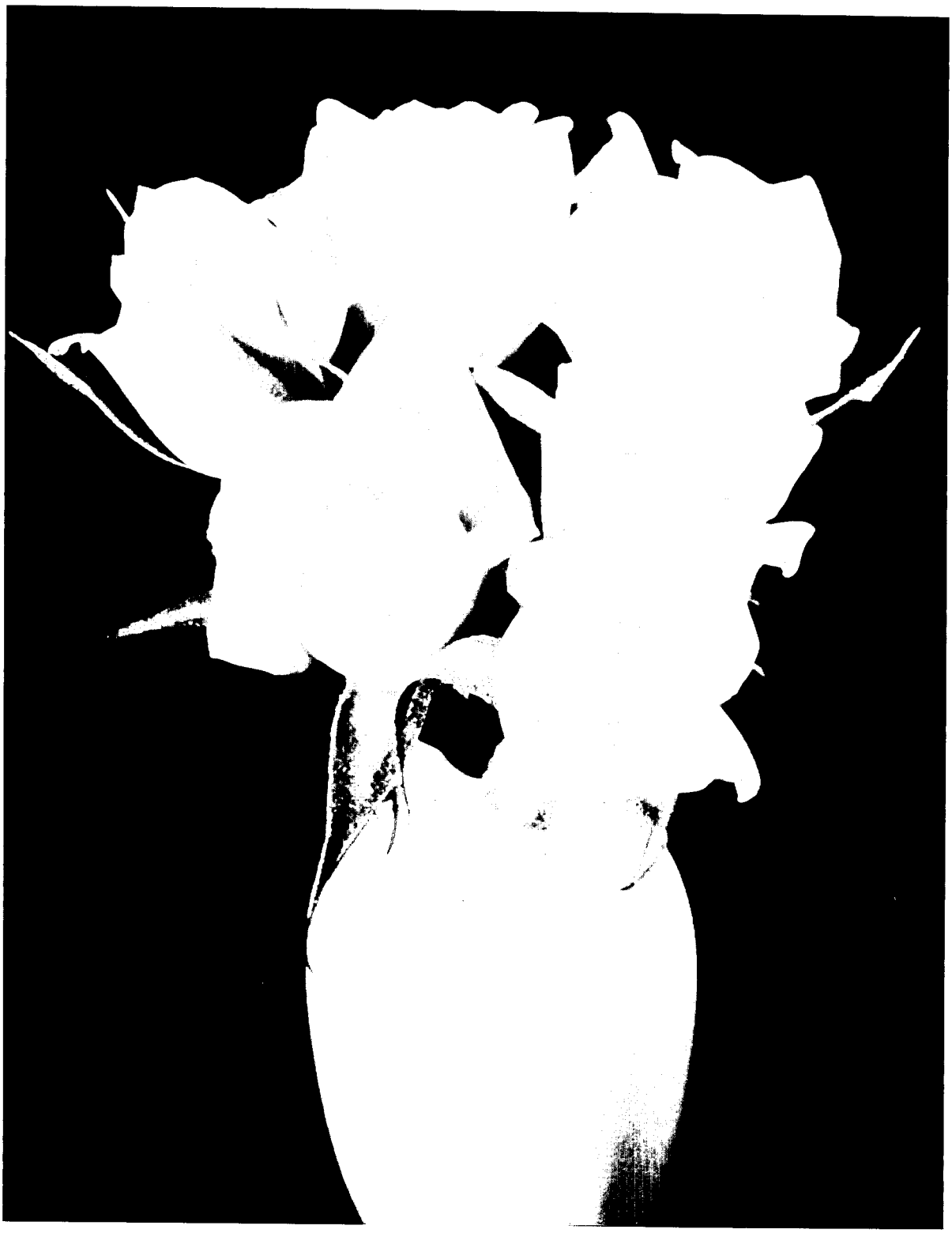

* * * * *